United States Patent [19]

Horiuchi et al.

[11] Patent Number: 5,166,537
[45] Date of Patent: Nov. 24, 1992

[54] PARTICLE ANALYZING METHOD AND DEVICE FOR REALIZING SAME

[75] Inventors: Hideyuki Horiuchi, Abiko; Hiroshi Ohki, Tsuchiura; Toshio Kaneko, Katsuta, all of Japan

[73] Assignee: Hitachi, Ltd., Tokyo, Japan

[21] Appl. No.: 628,018

[22] Filed: Dec. 17, 1990

[30] Foreign Application Priority Data

Dec. 22, 1989 [JP] Japan ................... 1-333848

[51] Int. Cl.⁵ ............................................. G01N 15/06
[52] U.S. Cl. ........................................ 250/573; 356/39
[58] Field of Search ................. 250/573, 574; 356/73, 356/335, 336, 337, 39, 40, 334

[56] References Cited

U.S. PATENT DOCUMENTS

| | | | |
|---|---|---|---|
| 2,656,508 | 10/1953 | Coulter | 324/71 |
| 4,263,508 | 4/1981 | Leary et al. | 356/335 |
| 4,341,993 | 7/1982 | Brunsting et al. | |
| 4,348,107 | 9/1982 | Leif | 356/72 |
| 4,374,644 | 2/1983 | Armstrong | 356/39 |
| 4,696,571 | 9/1987 | Goldberg et al. | 250/574 |

FOREIGN PATENT DOCUMENTS

| | | |
|---|---|---|
| 0068404 | 6/1982 | European Pat. Off. . |
| 58-179339 | 10/1983 | Japan . |
| 59-184841 | 10/1984 | Japan . |
| 60-115858 | 6/1985 | Japan . |
| 60-128327 | 7/1985 | Japan . |
| 61-502277 | 10/1986 | Japan . |

Primary Examiner—David C. Nelms
Attorney, Agent, or Firm—Fay, Sharpe, Beall, Fagan, Minnich & McKee

[57] ABSTRACT

According to the present invention, the accuracy of particle size histograms produced from data relating to an impedance variation (Coutler Counter Method) caused by particles passing between electrodes disposed on either side of an orifice through which the particles pass is improved by excluding false data from the data used in producing the histograms, the false data resulting from more than one particle being resident in the orifice at a given data collection time. The preferred embodiment employs a light detecting method and apparatus to detect false readings and to provide correction information used to correct data obtained by the Coulter Counter Method and apparatus.

9 Claims, 8 Drawing Sheets

PARTICLE ANALYZING METHOD AND DEVICE FOR REALIZING SAME

BACKGROUND OF THE INVENTION

The present invention relates to a particle analyzing method and device capable of measuring particles such as red blood cells, etc. to obtain various sorts of information on relevant particles, and, in particular to a particle analyzing method and device for measuring the size distribution of the particles.

Figure 1:
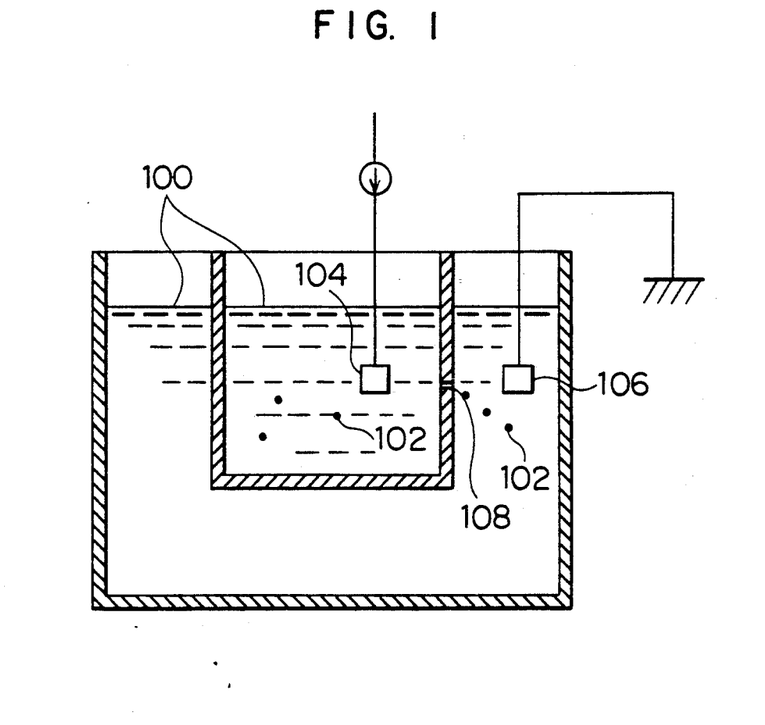
FIG. 1 is a cross-sectional view indicating the principle of the Prior Art Coulter counter method.

By a prior art particle analyzing method for analyzing extremely small particles it is known that, as indicated in FIG. 1, particles to be measured 102, are floated in an electrolytic solution such as a sodium chloride solution, etc., and are passed through an orifice 108. Electrodes 104 and 106 are disposed, on either of the orifice 108, to obtain information on the number and the size of the particles 102 by measuring variations in the electric impedance between the two electrodes 104 and 106 during passage of the particles 102 through the orifice (Coulter Counter Method). Refer to e.g. U.S. Pat. Nos. 2,656,508 and 4,348,107. Using the Coulter Counter method variations in the electric impedance are proportional to the volume of the particles and are used to produce a histogram of the particles. However, in order to correctly measure the variations in the electric impedance, it be necessary that the orifice sufficiently long in its axial direction. Further when the concentration of particles in an electrolytic solution containing particles is high, the that a plurality of particles will pass through the orifice simultaneously, increases.

Figure 2:
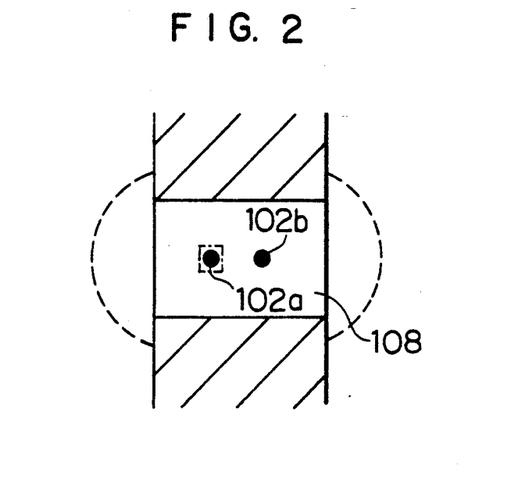
FIG. 2 is an enlarged cross-sectional view of an orifice.

That is, if a plurality of particles 102a and 102b exist in the orifice 108 simultaneously, as indicated in FIG. 2, the information obtained from the impedance at that time is as if there is only one particle and the volume thereof is the sum of the two particles 102a and 102b.

This problem of the simultaneous passage of two particles, called "coincidence", with respect to the information on the number of particles can be corrected mathematically, but similar correction of the information on the volume is not possible. This is because it is not possible to distinguish clearly whether the variations in the electric impedance due to the passage of particles are produced by one particle or by a plurality of particles.

Figure 3:
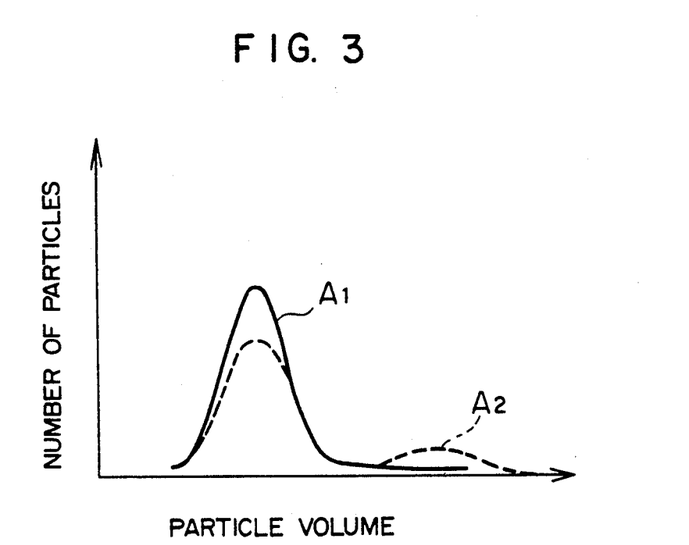
FIG. 3 shows a characteristic curve for explaining a problematical point of the particle volume histogram.

FIG. 3 shows an example of a particle volume histogram when particles having a uniform size at a high concentration are measured by the Coulter counter method. In this figure, the full line $A_1$ indicates a correct particle volume histogram, i.e. that obtained when no coincidence is produced. The broken line $A_2$ shows a particle volume histogram obtained in the case where coincidence occurs frequently. In the particle volume histogram indicated by the broken line $A_2$, individual particles having a particular volume, should appear in the neighborhood of the higher peak but, are distributed in the neighborhood of the second lower peak by the fact that a plurality of them pass through the orifice simultaneously. For this reason correct volume histogram information cannot be obtained.

As one method for solving the problem produced by coincidence, it is conceivable to reduce the concentration of particles. However, when the concentration of particles is reduced, the frequency of the passage of particles through the orifice is reduced, and a long time is necessary for measuring the impedance for an optional number of particles required for obtaining a desired counting precision, making the solution unpractical.

On the other hand, another method of correcting this error is known, where light scattering techniques are used for fine particle analysis. Refer to e.g. JP-A-Sho 60-115858. By this method, although the information on the size of particles can be obtained similarly, it is not possible to obtain any precise information on the volume with respect to the Coulter counter method. This is because measured data are influenced strongly by variations in the refractive index of particles themselves, intensity of light absorption, internal structure and shape. However, by this light scattering method (hereinbelow called light detecting method) it is possible to focus light into a spot at the focal point approximately as large as the particles by utilizing laser light as a light source. That is, since it is possible to make the measured domain as small as a square indicated by a dot-dashed line in FIG. 2, the probability is extremely small that more than two particles exist in the extremely small measured domain described above. Consequently this method has an advantage that the probability of measuring coincidence can be lowered with respect to the Coulter counter method.

As described above, the Coulter counter method and the light detecting method have different advantages.

SUMMARY OF THE INVENTION

A first object of the present invention is to trace a precise volume histogram by, excluding influences of the coincidence of a plurality of particles in an orifice, using the Coulter counter method.

A second object of the present invention is to make it possible to compare the volume histogram, from which the influences of coincidence are excluded, with a volume histogram obtained by utilizing the light detecting method.

In order to achieve the above first object, according to the present invention, a light detecting system capable of detecting the coincidence of a plurality of particles with a very high precision is added to a Coulter counter system and more precise information on the volume of particles is obtained by excluding data relating to coincidence from data obtained by the Coulter counter method using information obtained by the light detecting method.

Further, the total number of particles passing through the orifice is compared with the number of particles, passing separately therethrough, and the histogram obtained by excluding the data relating to coincidence is corrected on the basis of the comparison result.

In order to achieve the above second object, a volume histogram is formed by excluding data relating to coincidence from the data obtained by the Coulter counter method and, at the same time, a volume histogram is formed by the light detecting method so that these two histograms can be compared with each other.

DESCRIPTION OF THE PREFERRED EMBODIMENTS

Hereinbelow several embodiments of the present invention will be explained, referring to the attached drawings.

Figure 5:
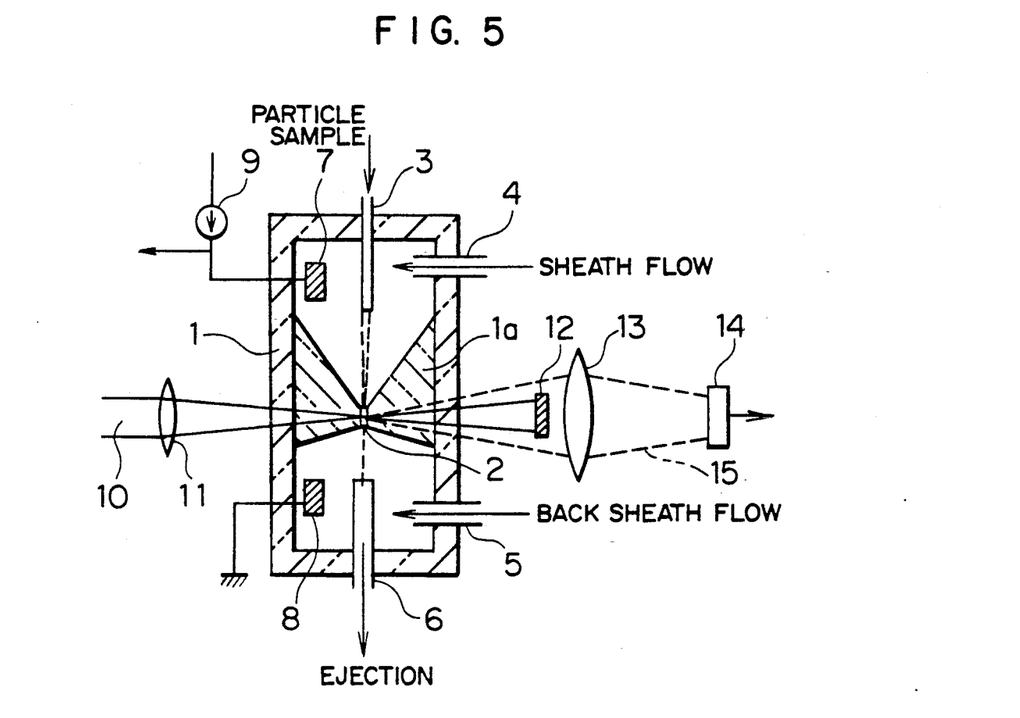
FIG. 5 is a cross-sectional view indicating the internal structure of a flow through cell used in a particle analyzing device according to the present invention.

At first the construction of a particle detecting section will be explained, referring to FIG. 5, in which reference numeral 1 is a flow through cell, which has the form of a parallelepipedic box made of transparent wall members, e.g. glass. The flow through cell 1 is so disposed that the up and downward direction in FIG. 5 is the longitudinal direction. In the interior of the flow through cell 1 a transparent wall portion 1a is formed at an approximately central portion in the up and downward direction. An orifice 2 is formed at the center of this transparent wall portion 1a. Two chambers are formed, one above and one below the transparent wall portion 1a within the flow through cell 1. A conical recess portion is formed on the upper surface of the transparent wall portion 1a and an inlet portion of the orifice 2 described above is formed at the narrow portion of this conical recess portion. A particle sample, the object to be measured, is injected through a nozzle 3 disposed in the upper wall portion. The particle sample pushed out from the nozzle 3 is surrounded by a sheath flow injected through a sheath flow injection opening 4 and passes through the orifice 2 described above. The flow, which has passed through the orifice 2, is surrounded further by a back sheath flow injected through a back sheath flow injection opening 5 and ejected through an outlet 6 outside of the flow through cell 1.

Both the sheath flow and the back sheath flow described above, which surround the particle sample, are electrolytic. For example, a physiological saline solution is used therefor. In the upper and the lower chamber within the flow through cell 1 are disposed electrodes 7 and 8, respectively. The electrode 7 is connected with a constant current source 9 and the electrode 8 is grounded. When the flow through cell 1 is filled only with the sheath flows a particular electric impedance is produced between the electrodes 7 and 8. When a particle sample injected through the nozzle 3 passes through the orifice 2, it gives rise to a phenomenon that the electric impedance between the electrodes 7 and 8 varies. By using these variations in the electric impedance it is possible to obtain information on the size of the particle sample that has passed through the orifice 2.

The size of the orifice 2 described above depends on the particles to be measured. For example, for particles of about 10 μm it is thought that a cross-section of 50 μm×50 μm and a length of about 60 μm are suitable.

Figure 6:
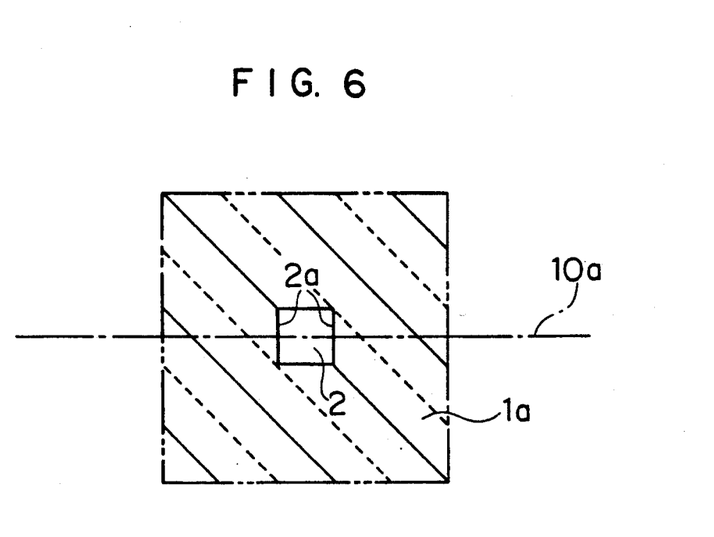
FIG. 6 is a cross-sectional view indicating the shape of the orifice.

As indicated in FIG. 6, in the orifice 2, the wall surfaces 2a intersecting the optical axis 10a of the laser light (described later) should be flat in order to prevent refraction of the laser light.

The measurement of the variations in the electric impedance is effected by making a constant current flow between the electrodes 7 and 8 by means of the constant current source 9 and by transforming the variations in the electric impedance into voltage variations. Since the variations in the electric impedance are produced in the neighborhood of the inlet and the outlet of the orifice 2, the effective length of the orifice is greater than the geometrical length thereof. Consequently the probability of taking plural particles simultaneously in the orifice 2 (coincidence), and considering as correct data using the Coulter counter method is higher than that obtained by using the detecting method utilizing light scattering (described later).

In the construction indicated in FIG. 5, in addition to the particle detecting system utilizing electric impedance variations (electric impedance variation detecting system) there is disposed another particle detecting system utilizing light scattering (light scattering detecting system). Reference numeral 10 represents a laser light beam outputted by a laser light source not shown in the figure and the laser light beam 10 is set by a convergence lens 11 so that the focal point thereof is formed at the center point of the orifice 2. The laser light beam is scattered when the particle sample surrounded by the sheath flow passes through the position of the focal point in the orifice. On the other side of the flow through cell 1 there are disposed a blocker 12, a focusing lens 13 and a photodetector 14. The laser light beam not scattered is blocked by the blocker 12 and cannot advance beyond it. On the other hand, scattered light 15 is gathered by the focusing lens 13 and the optical information thus obtained is transformed into an electric signal by the photodetector 14. Since the laser light beam can be focused by the action of the convergence lens 11 into a spot as small as the particle sample (object to be measured), the probability of detecting the coincidence of a plurality of particles in the orifice 2 is fairly high.

Figure 7:
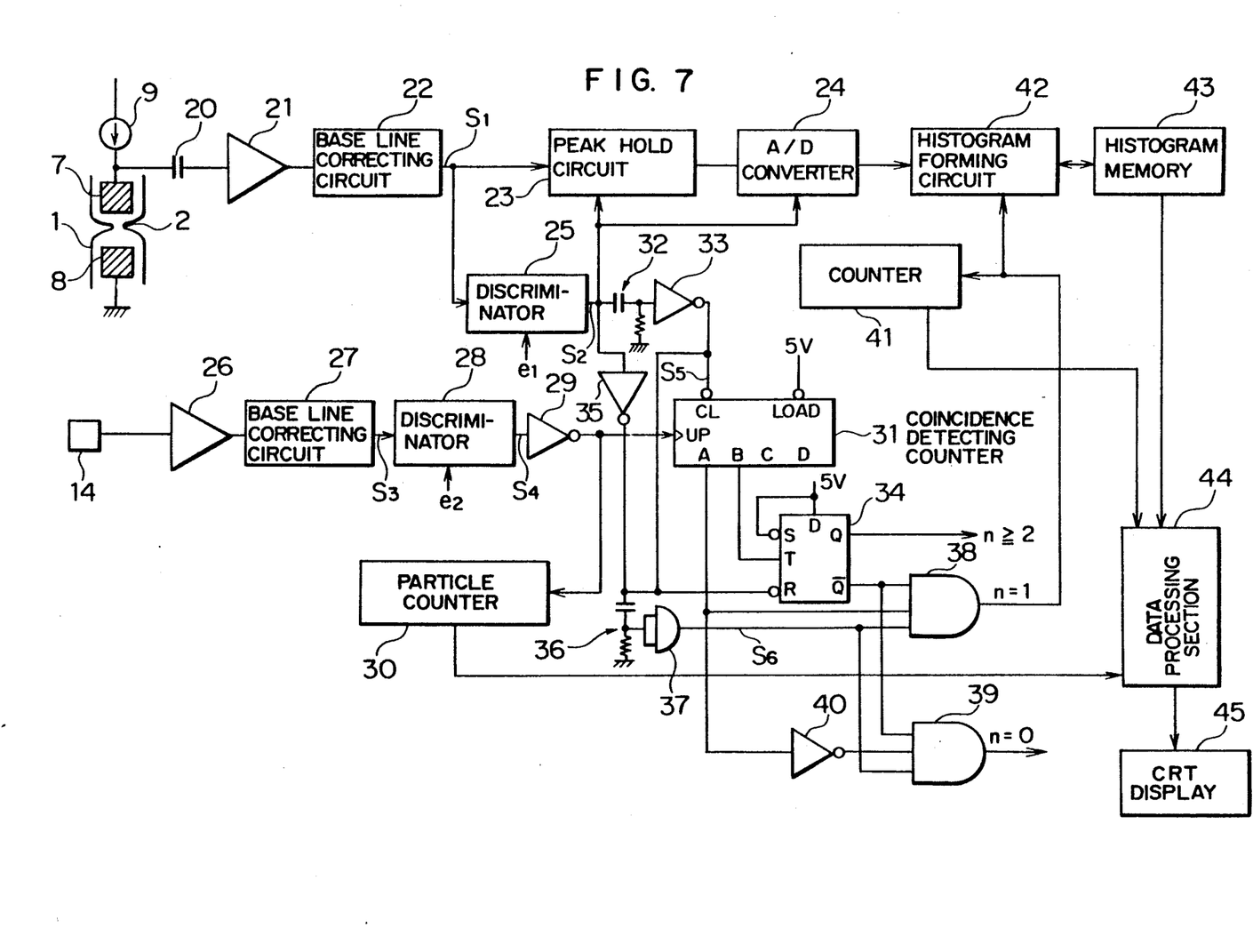
FIG. 7 is a diagram indicating the construction of a signal processing circuit.
Figure 8:
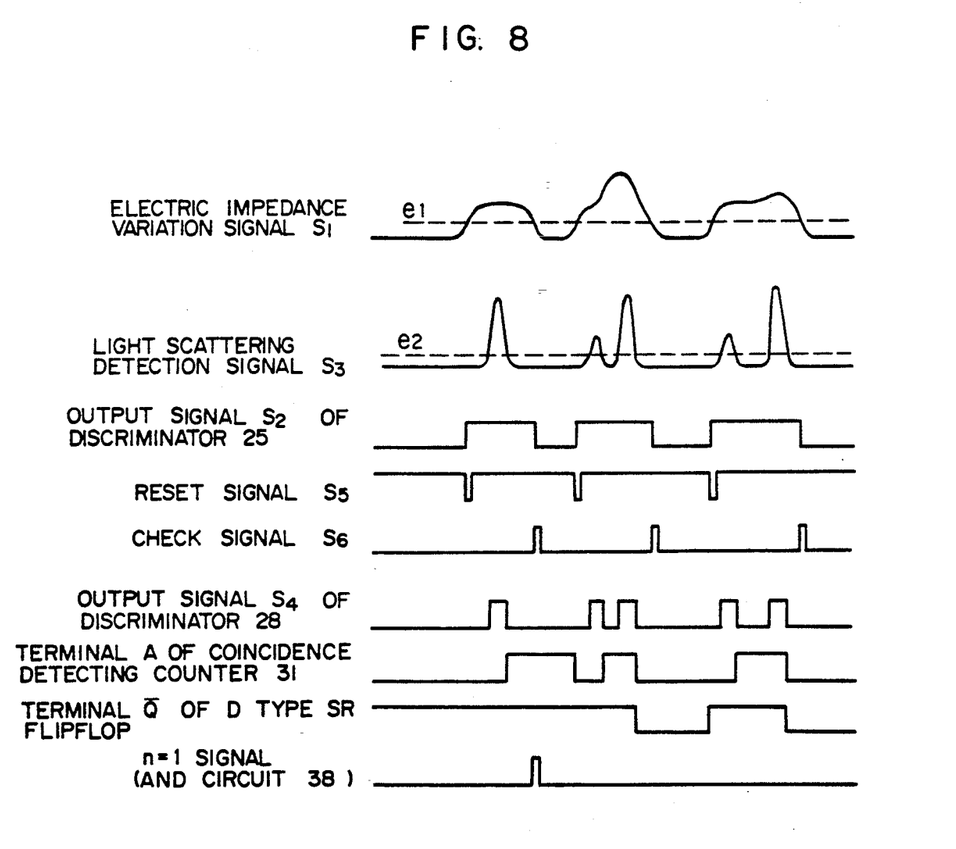
FIG. 8 is a timing chart showing signal states of different parts in the signal processing circuit.

Now the construction and the operation of a signal processing circuit will be explained, referring to FIGS. 7 and 8. FIG. 7 indicates the circuit construction and FIG. 8 is a timing chart of signals produced in different parts of the circuit.

In FIG. 7, reference numeral 1 is the flow through cell; 2 is the orifice; 7 and 8 are electrodes; 9 is a constant current source; and 14 is a photodetector. These are identical to the elements of FIG. 5. A particle detection signal obtained by transforming a variation in the electric impedance due to the passage of a particle into an electric signal, whose DC component is cut by a capacitor 20, is amplified to a required level by an amplifier 21 and supplied to a base line correcting circuit 22. The base line correcting circuit 22 has a clamping function and a function to set the voltage of the base line at 0 V by regulating the circuit so that the lower limit of the signal corresponding to the particle detection is 0 V. The output signal $S_1$ of the base line correcting circuit 22 thus obtained is divided into two routes, which are subjected to signal processing separately. One of them is a circuit route consisting of a peak hold circuit 23 and an A/D converter 24. The peak value of the signal $S_1$ corresponding to the particle detection is read out by this circuit and this peak value is converted into a digital value. The other signal is supplied to a discriminator 25 and this discriminator 25 has a comparing function to recognize a particle detection signal above a certain level $e_1$ as a particle pulse. The output signal $S_2$ of this discriminator 25 is supplied to the peak hold circuit 23 and the A/D converter 24 to control respective operations.

On the other hand, in the light scattering detecting system, the detection signal $S_3$ of the photodetector 14 is amplified by an amplifier 26 and regulated by a base line correcting circuit 27 so that the base line thereof is at 0 V. Among signals thus transformed, those having amplitudes above a certain level $e_2$ are considered as particle pulses and taken out by a discriminator 28. A particle detection pulse $S_4$ outputted by the discriminator 28 is inverted by an inverter 29 and inputted in a particle counter 30 in one route, while it is inputted in a coincidence detecting counter 31 in the other route.

The pulse signal $S_2$ outputted by the discriminator 25 generates a signal corresponding to the rise thereof in a differentiating circuit 32. This signal is inverted by an inverter 33 and inputted as a reset signal $S_5$ in the coincidence detecting counter 31 and a D type SR flipflop 34. Another signal corresponding to the fall of the pulse signal $S_2$ is formed by an inverter 35, a differentiating circuit and an AND circuit 37 and used as a check signal $S_6$. By using this check signal $S_6$ it is possible to judge how many light scattering signals there are in the electric impedance variation detecting signals with the timing, where this signal is "1".

The function of the coincidence detecting counter 31 is to count how many particle detection pulses $S_4$ are generated in the light scattering detecting system, while the output of the discriminator 25 is 1, or, in other words, while a particle sample passes through the orifice 2 and a particle detection pulse $S_2$ is generated in the electric impedance detecting system. The count value of particle detection pulses $S_4$ is outputted by using terminals A, B, C and D of coincidence detecting counter 31. The number of the particle detection pulses $S_4$ is reflected terminals A, B, C and D. In the count value of the coincidence detecting counter 31 the terminals A, B, C and D represent the first, second, third, and the fourth bit, respectively. Consequently, in the counting operation of the coincidence detecting counter 31, when the count value changes from 1 to 2, the terminal B varies from "0" to "1". Since the output of the terminal B is inputted in the D type SR flipflop 34, the flipflop 34 is set at the point of time of the rise when the terminal B changes from "0" to "1" and the output Q changes from "0" to "1". Therefore, if the state of the output Q is "1", it can be understood that the state of the count value n of the coincidence detecting counter 31 is given by $n \geq 2$.

Further, it is when each of the outputs $\overline{Q}$ of the flipflop 34, the terminal A of the coincidence detecting counter 31 and the check signal outputted by the AND circuit 37 are "1" that the output of a 3-input AND circuit 38, in which the output $\overline{Q}$ of the flipflop 34 is inputted, is "1". In this case the count value n of the coincidence detecting counter 31 is equal to 1. In this way it is understood that, when the output of the AND circuit 38 is "1", it is not due to coincidence but due to a single particle. The output $\overline{Q}$ of the flipflop, the output of the AND circuit 37 and the output of the coincidence detecting counter 31 through the terminal A inverted by the inverter 40 are inputted in the 3-input AND circuit 39 and it is in the case where count value of the coincidence detecting counter 31 $n = 0$ and erroneous operation is produced in the electric impedance variation detecting system due to noise, etc. that the output of the AND circuit 39 is "1".

The output of the AND circuit 38 described above is given to a counter 41 and a histogram forming circuit 42. When the count value of the coincidence detecting counter 31 is 1 and the output of the AND circuit 38 is "1", the counter 41 performs a count up operation and at the same time the histogram forming circuit 42 performs a particle volume histogram forming operation. The histogram forming circuit 42 reads out the output of the A/D converter 24 as histogram forming data to form a histogram. The result thus obtained is stored in a histogram memory 43. When one measurement of the particle sample in the orifice 2 of the flow through cell 1 is terminated, the count value of particles at that time is recorded in the particle counter 30; the count value of individual particles where no coincidence is produced, is recorded in the counter 41; and the data of the particle volume histogram obtained by electric impedance variation signals recognized as those produced by individual particles are recorded in the histogram memory 43. The data stored in the particle counter 30, the counter 41 and the histogram memory 43 are inputted in a data processing section 44, processed therein, and the result of the processing is displayed on a CRT display 45. Further, when desired, the result of the processing is outputted to a printer or an external memory device not shown in the figure.

According to this embodiment, a particle volume histogram only for individual particles is formed by excluding particle volume histogram data obtained when coincidence occurs by using data relating to coincidence obtained by the light scattering detecting system and using it to correct particle volume histogram data obtained by the electric impedance variation detecting system passing through the orifice 2.

Figure 4:
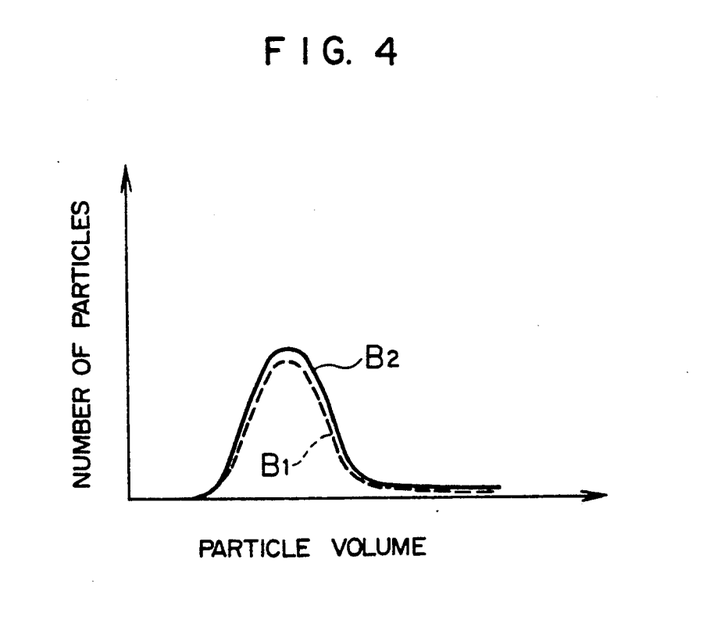
FIG. 4 shows a histogram traced by an embodiment of the present invention.

The result of a histogram detected under the same conditions as those used for FIG. 3 but employing the present invention is indicated by a broken line curve $B_1$ in FIG. 4. The shape of the peak indicated by this broken line $B_1$ is identical to the shape of the higher peak indicated by the broken line curve $A_2$ in FIG. 3.

Figure 9:
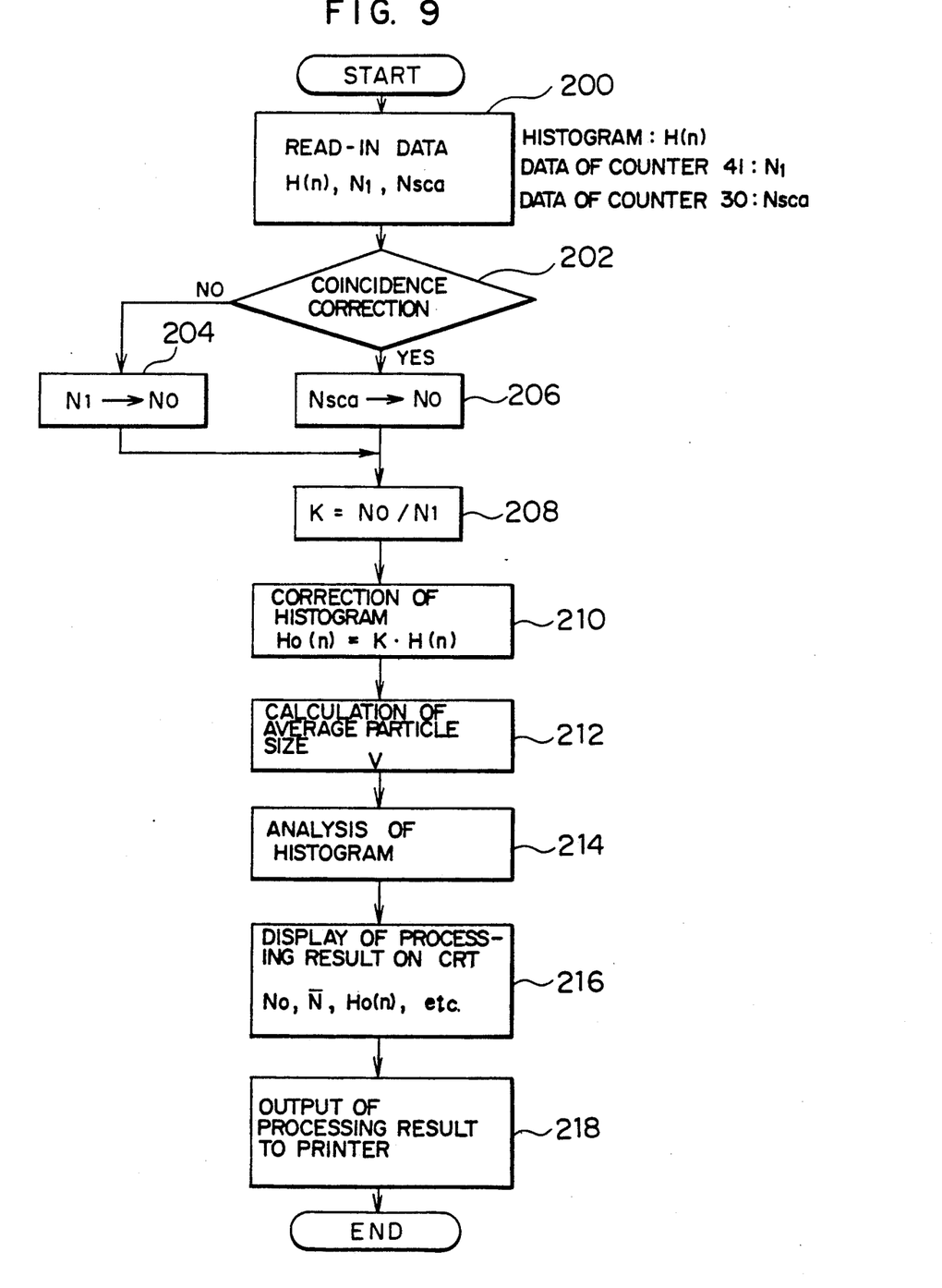
FIG. 9 is a flow chart showing the operation of a data processing section.

FIG. 9 shows an example of how data is processed in the data processing section described above.

At first, in Step 200, histogram data H(n) indicating the relation between the particle volume and the number of particles is read out from the histogram memory 43. These histogram data H(n) are obtained by excluding the data relating to coincidence.

In Step 200, further data $N_1$ of the counter 41 and data $N_{sca}$ of the counter 30 are read out. The data $N_1$ represents the number of particles, which have passed individually through the orifice and the data $N_{sca}$ indicates the total number of particles counted by the light detecting method (=number of individual particles + number of coincident particles).

When the mode for excluding influences of coincidence is not selected by using an external key not shown in the figure (Step 200), $N_1$ which represents data indicating the number of individual particles, is $N_0$ (Step 204). When the mode for correcting the influences of the coincidence to approach the true value is selected (Step 202), $N_{sca}$ representing the total number of passing particles is $N_0$ (Step 206).

Next the ratio K of $N_0$ to $N_1$ representing the data indicating the number of individual particles is calculated (Step 208). The ratio K is multiplied by the histogram data H(n) (Step 210). Here, when the process passes through step 204, i.e. when the data relating to coincidence is excluded, K=1 and thus $H_0(n)=H(n)$. These histogram data are indicated by the broken line $B_1$ in FIG. 4. On the other hand, when the process passes through Step 206, they are indicated by the full line $B_2$ in the figure. In FIG. 4, the number of particles corresponding to the part enclosed by the broken line $B_1$ and the full line $B_2$ is equal to the number of particles considered as those counted by coincidence.

In Step 212, the average particle size V is calculated. In Step 214, the histogram data $H_0(n)$ are compared with the data base previously stored and analyzed in this way.

In Step 216, $N_0$, $\overline{V}$, $H_0(n)$ and other necessary data obtained as the result of the processings described above are displayed on a CRT. Further, they are printed out by means of a printer not shown in the figure (step 218).

The output Q of the flipflop 34 and the output of the AND circuit 39 are used also for data processing as needed.

Next, an embodiment of the present invention, modified on the basis of the construction of the fundamental embodiment described above, will be explained.

A signal processing circuit can be constructed by adding a circuit for tracing the volume histogram based on the light scattering detecting system to the circuit of FIG. 7.

Figure 10:
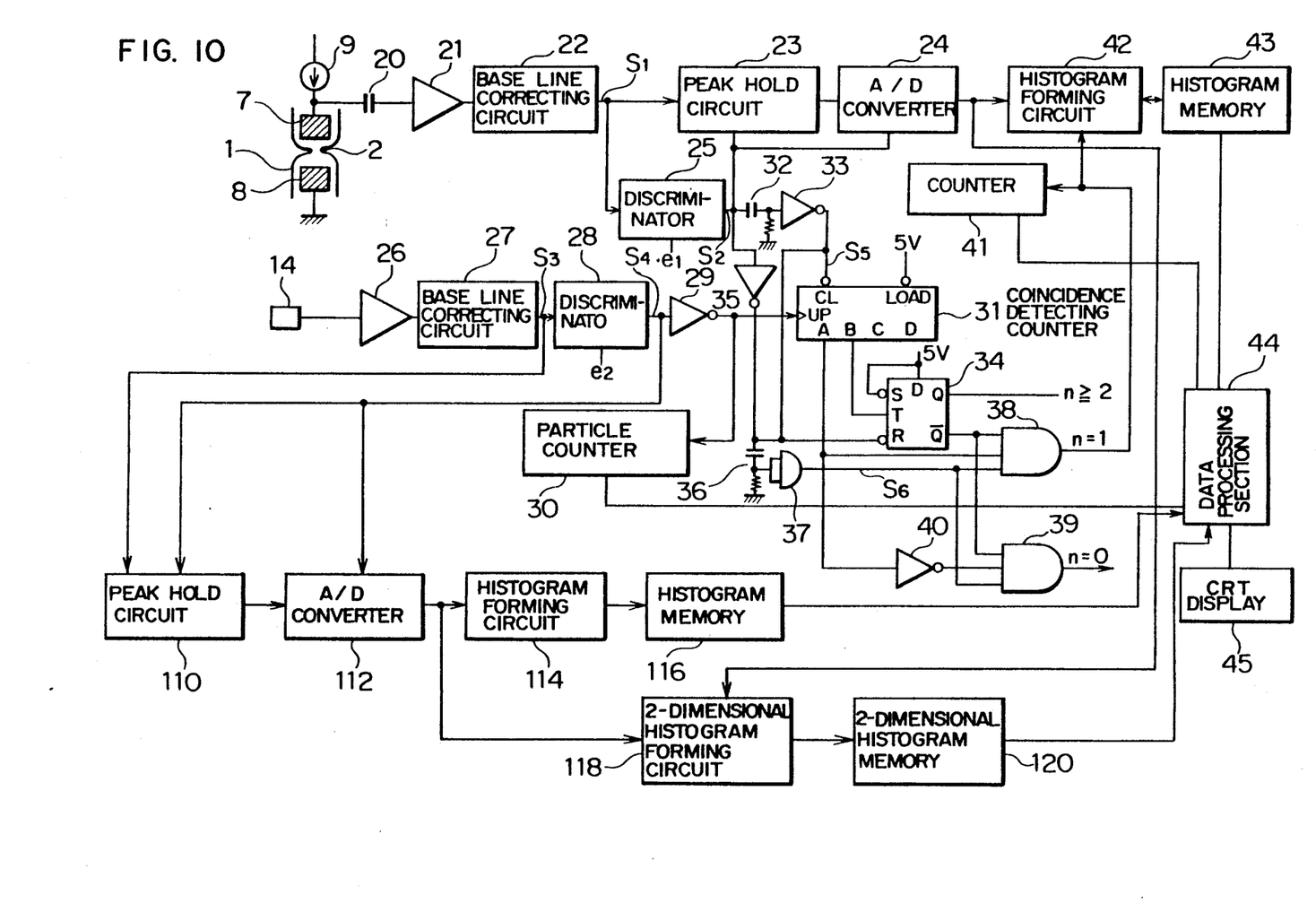
FIG. 10 is a diagram indicating the construction of a signal processing circuit of an alternative embodiment of the present invention.

That is, as indicated in FIG. 10, there are disposed a peak hold circuit 110, an A/D converter 112, a histogram forming circuit 114 and a histogram memory 116 in line after the base line correcting circuit 27. The histogram memory 116 is connected with the data processing section 44. Similarly there is disposed a two-dimensional histogram forming circuit 118 and histogram data are prepared by using A/D conversion output data from the two systems. They are transmitted to the data processing section 44 after having been stored in a two-dimensional histogram memory 120. The output signal $S_4$ of the discriminator 28 is inputted in the peak hold circuit 110 and the A/D converter 112 to control the respective operation.

Also, in the particle analyzing device of the present embodiment, as it is clearly seen in the embodiment described above, there is no problem of coincidence in the electric impedance variation detecting system. Since it is not influenced by the coincidence of particles in the electric impedance variation detecting system, which was a problem heretofore, it is possible to obtain precise shape information on the particle sample by comparing the particle volume information obtained by measuring variations in the electric impedance with the particle volume information obtained by measuring light scattering. The analysis of the two dimensional particle volume histogram obtained by the electric impedance variation detecting system and the light scattering detecting system can be effected easily by displaying them on a same CRT display 45. Concerning this technique, refer to JP-B-Sho 61-502277 and JP-A-Sho 59-184841.

The signal processing circuit indicated in FIG. 7 may be constructed so as to have a window comparing function, by which two comparison levels $e_2$ and $e_3$ are set in the discriminator 28 of the light scattering detecting system and only light scattering signals, which are in the level region between $e_2$ and $e_3$, are used. If the comparing level $e_3$ is set at such a level that the coincidence of the particle sample can be detected in the light scattering detecting system, it is possible to raise further the precision of the formation of the particle volume histogram in the first embodiment described above. Further it is possible also to limit the size of particles to be measured by setting the level $e_3$ so that great particles, which are outside the range of particles to be measured, are excluded.

Figure 11:
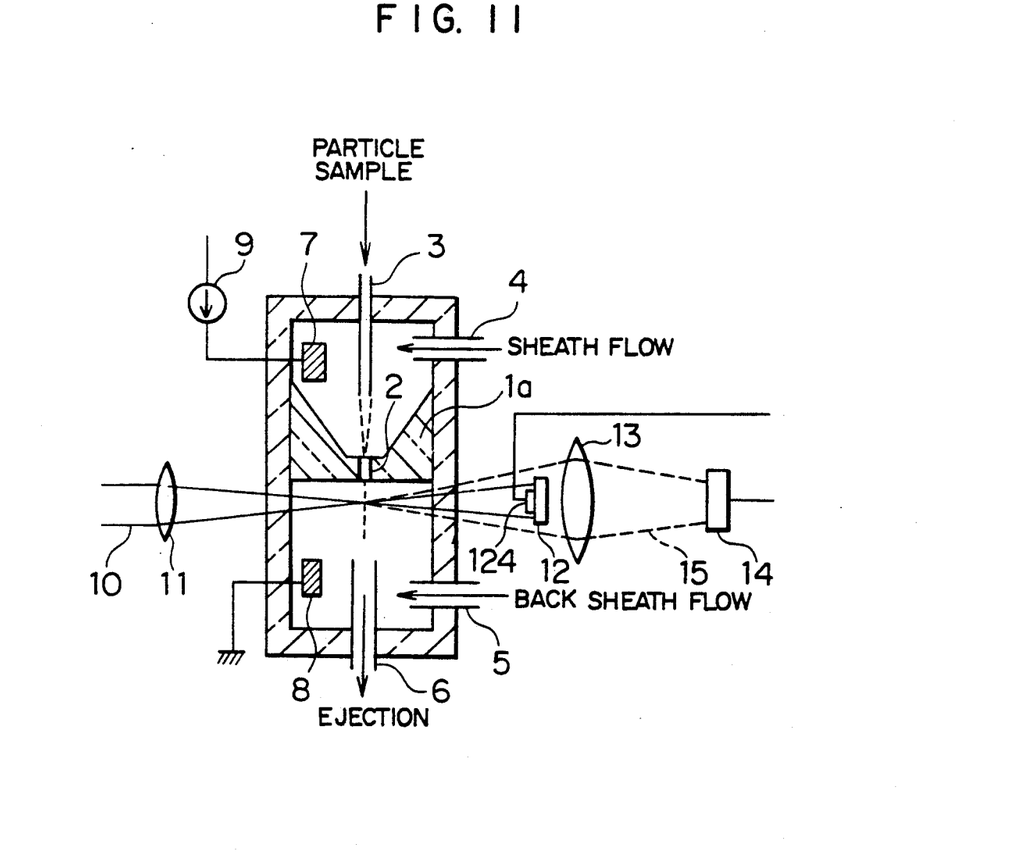
FIG. 11 is a cross-sectional view indicating the internal structure of a flow through cell of an alternate embodiment of the present invention.

Although, in the construction indicated in FIG. 5, the laser light beam 10 is focused at the central position of the orifice 2, it is possible also to set the focus position of the laser light beam outside of the inlet or outlet of the orifice 2, as indicated in FIG. 11. In this case, it is necessary to adjust the timing between the particle detection pulse obtained by the electric impedance variation detecting system and the particle detection pulse obtained by the light scattering detecting system by disposing a delaying circuit, etc. to adjust the timing in the signal processing circuit.

In FIG. 11, the features substantially identical to those indicated in FIG. 5 are referred to by the same reference numerals and explanation thereof will be omitted. Reference numeral 124 in the figure represents a photodetector, which detects the presence or absence of the absorption at a specified wavelength due to particles.

In a flow through cell having such a construction, since the laser light beam 10 doesn't pass through the orifice 2, the cross section of the orifice can be circular. Such an orifice 2 can be formed by means of a usual laser working machine etc. and therefore it can be formed more easily in a shorter time than the orifice indicated in FIG. 6. In this way fabrication cost of the flow through cell is lowered.

In the signal processing circuit indicated in FIG. 10, it is possible also to construct it so as to form a relation of magnitude of different signals or a 2-dimensional histogram by analyzing simultaneously the electric impedance variation detection signal (due to individual particles obtained by excluding signals relating to coincidence and the light scattering detection signal and to effect the sorting and the identification of particles to be measured by using these results. Since the light scattering detection signal not only includes size information of the particle sample, but also varies, depending on differences in the shape, the refractive index, the internal structure, etc., it is possible to identify the particles on the basis of these differences.

The optical system used in the light scattering detecting system in the embodiments described above is a forward scattering optical system. An effect similar to that obtained in the embodiments described above can be obtained, even if they are constructed by using an orthogonal scattering optical system or a backward scattering optical system, or further a light absorbing optical system or a fluorescent scattering optical system apart therefrom. In particular, since depolarization information by orthogonal scattering and fluorescent scattering information are influenced strongly by differences in the internal structure of the particle to be measured, they are useful for sorting and identification of the particle sample.

Although, in the embodiments described above, the kind of the particles, which are objects to be measured, is not specified, e.g. red blood cells, white blood cells, platelets, etc. can be examples of the particles. By means of the present device it is possible to obtain very precisely the count value, information of volume distribution analysis and information on average blood cell volume of these particles. In particular, in the case where red blood cell volume histogram is measured, when it is measured only by the Coulter counter method, a pseudo peak due to the simultaneous passage of two particles appears at a position corresponding to twice the volume of a red blood cell. On the contrary, by the construction of the particle analyzing device according to the present invention, since coincidence is detected by the light scattering detecting system and excluded from the data for forming the volume histogram, such a problem is not produced.

Furthermore the circuit construction indicated in FIG. 7 is only one embodiment. Any circuit can be used, if it can realize a similar function. That is, any circuit construction can be adopted if it is a circuit capable of judging light scattering detection signal that only one particle exists in a particle pulse, the particular pulse provided by the Coulter counter method.

We claim:

1. A particle analyzing method comprising:
   providing an orifice having an inlet side and an outlet side;
   providing a pair of electrodes between which an impedance can be measured, one of said electrodes adjacent to said inlet side and the other of said electrodes adjacent to said outlet side of said orifice;
   providing optical means associated with said orifice including a light source and a light detector capable of sensing variations in the light from said light source passing near said orifice to said detector;
   passing particles in solution through said orifice;
   detecting impedance variations between said electrodes cause by the passage of said particles through said orifice;
   measuring light variations caused by the passage of said particles between said light source and said light detector;
   determining whether substantially one particle or a plurality of particles is present in said orifice during said detecting by using information obtained during said measuring; and
   forming a first particle volume histogram using data obtained from said detecting step, said data modified by information obtained from said measuring and said determining so that said histogram is produced by data obtained from said detecting but excluding data collected during said detecting when more than one particle was present in the said orifice.

2. The particle analyzing method according to claim 1, wherein said measuring step further comprises counting the total number of particles passing through said orifice ($N_{sca}$);
   wherein said determining includes the step of providing the number of particles passing through said orifice individually ($N_1$); and
   wherein said step of forming a particle volume histogram includes the step of calculating a correction factor K where $K = N_{sca}/N_1$, said histogram formed by correcting the result of said detecting step using correction factor K.

3. The particle analyzing method according to claim 1, further comprising the step of forming a second particle volume histogram using only the result of said light measuring step; and
   classifying and identifying said particle by comparing said first particle volume histogram and said second particle volume histogram.

4. A particle analyzing method according to claim 1, wherein said particles to be analyzed are blood components comprising red blood cells, white blood cells, and platelets.

5. A particle analyzing method according to claim 1, wherein said light measuring step is conducted using light focused on said orifice, the flow of said particles acting to disturb said light to provide an output.

6. The particle analyzing method according to claim 1, wherein the cross-section of said orifice in the direction perpendicular to the passage of said particles in solution is substantially circular; and
   said light focused on said particles in solution is focused near said inlet or said outlet of said orifice but not in said orifice during said light measuring step.

7. The particle analyzing method according to claim 1, wherein said light measuring step employs laser light.

8. The particle analyzing method according to claim 1, wherein said step of light measuring is conducted using a light detector capable of detecting forward scattered light, sideward scattered light, backward scattered light, fluorescent scattered light, or absorbed light.

9. A particle analyzing device comprising:
   an orifice having an inlet side and an outlet side through which particles in solution can flow;
   a pair of electrodes between which an impedance can be measured, one of said electrodes adjacent to said inlet side, the other of said electrodes adjacent to said outlet side of said orifice, passage of said particles between said electrodes providing an impedance variation depending on the size and volume of the particle;
   optical means associated with said orifice including a light source and a light detector capable of sensing variations in the light disturbed by said particle flow, said variations caused by the presence of particles in said flow, said optical means capable of determining whether substantially one particle or a plurality of particles is present in said orifice during the time in which said electrodes sense the size and volume of said particles; and
   means for forming a particle volume histogram by using information provided by said impedance measuring electrode, said information modified by data collected from said optical means so that the information used for forming said particle volume histogram includes information obtained by the passage of single particles through said orifice.

* * * * *